United States Patent
Kibble

(10) Patent No.: US 11,823,787 B2
(45) Date of Patent: Nov. 21, 2023

(54) SYSTEMS AND METHODS FOR TRANSFERRING MEDICAL IMAGE RECORDS USING A PREFFERRED TRANSFER PROTOCOL

(71) Applicant: FUJIFILM MEDICAL SYSTEMS U.S.A., INC., Morrisville, NC (US)

(72) Inventor: Gary Kibble, Cary, NC (US)

(73) Assignee: Fujifilm Healthcare Americas Corporation, Lexington, MA (US)

( * ) Notice: Subject to any disclaimer, the term of this patent is extended or adjusted under 35 U.S.C. 154(b) by 720 days.

(21) Appl. No.: 16/369,782

(22) Filed: Mar. 29, 2019

(65) Prior Publication Data

US 2020/0312439 A1    Oct. 1, 2020

(51) Int. Cl.
*G16H 30/20* (2018.01)
*G16H 30/40* (2018.01)

(52) U.S. Cl.
CPC ............ *G16H 30/20* (2018.01); *G16H 30/40* (2018.01)

(58) Field of Classification Search
USPC ....................................................... 705/2–3
See application file for complete search history.

(56) References Cited

U.S. PATENT DOCUMENTS

| | | | |
|---|---|---|---|
| 6,275,869 B1 * | 8/2001 | Sieffert | .................... H04L 29/06 719/321 |
| 6,564,256 B1 | 5/2003 | Tanaka | |
| 2002/0073429 A1 | 6/2002 | Beane et al. | |
| 2004/0249677 A1 * | 12/2004 | Datta | ..................... G16H 10/60 705/3 |
| 2008/0189496 A1 * | 8/2008 | Raczynski | ............. G16H 30/20 711/161 |
| 2012/0183191 A1 * | 7/2012 | Nakamura | ............. G16H 30/40 382/128 |
| 2014/0101273 A1 * | 4/2014 | Logan | .................... H04L 51/02 709/206 |
| 2014/0142984 A1 | 5/2014 | Wright et al. | |

(Continued)

FOREIGN PATENT DOCUMENTS

| | | |
|---|---|---|
| CN | 101398869 A | 4/2009 |
| WO | WO 2002/039364 A2 | 5/2002 |

OTHER PUBLICATIONS

Varma, "Managing DICOM images: Tops and tricks for the radiologist," Indian Journal of Radiology and Imaging, 22(1), p. 4-13 (Year: 2012).*

(Continued)

*Primary Examiner* — Jason S Tiedeman
(74) *Attorney, Agent, or Firm* — Baker Botts L.L.P.

(57) ABSTRACT

A method for transferring a medical image record including, receiving, by one or more computing devices and from a client device of a first user, a query for the medical image record stored within a record storage system, the medical image record having one or more characteristics; selecting, by the one or more computing devices, a transfer protocol for transferring the medical image record from the record storage system based on at least one of the characteristics of the medical image record; transferring, by the one or more computing devices, the medical image record using the transfer protocol; and sending the medical image record to the client device of the first user for display.

16 Claims, 2 Drawing Sheets

(56) References Cited

U.S. PATENT DOCUMENTS

2018/0239868 A1* 8/2018 Kopylov ............... G16H 30/20
2019/0189282 A1* 6/2019 Noro ..................... G16H 40/63

OTHER PUBLICATIONS

DICOM, https://www.dicomstandard.org/using/dicomweb, last visited Aug. 7, 2023.*
Bidgood, Jr. et al., "Understanding and Using DICOM, the Data Interchange Standard for Biomedical Imaging," Journal of the American Medical Informatics Association, vol. 4, No. 3, 1997, pp. 199-212.
International Search Report and Written Opinion of the International Searching Authority dated Apr. 24, 2020 for International Application No. PCT/US2020/015783.

* cited by examiner

SYSTEMS AND METHODS FOR TRANSFERRING MEDICAL IMAGE RECORDS USING A PREFFERRED TRANSFER PROTOCOL

BACKGROUND

I. Field of Disclosed Subject Matter

The disclosed subject matter is directed to systems and methods for transferring digital records, for example, medical image records, and more specifically, Digital Imaging and Communications in Medicine (DICOM) objects. The medical image records can be transferred using a specifically selected transfer protocol, for example a DICOM messaging protocol or a DICOM web services protocol.

2. Description of Related Art

In medical imaging, Picture Archiving and Communication Systems (PACS) are a combination of computers and networks dedicated to the storage, retrieval, presentation, and distribution of images. While images may be stored in a variety of formats, a common format for image storage is Digital Imaging and Communications in Medicine (DICOM). DICOM is a standard in which, among other things, medical images and associated meta-data can be communicated from imaging modalities (e.g., X-ray, computed tomography (CT), and magnetic resonance imaging (MRI) apparatuses) to the PACS for storage and from PACS to a client device for viewing by a user, such as medical personnel.

For many years, the standard for transferring medical image records stored in PACS was a DICOM messaging protocol, which provides the communications framework for DICOM services. For example, DICOM operations C-MOVE or C-GET could be used to transfer medical image records over Transmission Control Protocol (TCP) connections.

With the introduction of DICOM PS3.18—Web Services, an alternative object acquisition protocol using web services (e.g., HyperText Transfer Protocol (HTTP) connections or HyperText Transfer Protocol Secure (HTTPS) connections, collectively "HTTP/S") was introduced. Particularly, new web-based operations, such as Web Access for DICOM Objects (WADO) operations, including WADO-RS or WADO-URI, were intended to replace the C-MOVE and C-GET operations.

The two protocols do not integrate. A user either uses TCP for DICOM massaging or HTTP/S for DICOM web services. In general, DICOM web services are better suited for quickly moving small amounts of data, such as a single medical image, but DICOM messaging is better suited for moving large amounts of data, such as a DICOM Study with thousands of medical images.

Accordingly, there is a need for systems and methods for more efficiently transferring medical image records, such as DICOM objects, by using the appropriate transfer protocol based upon characteristics of the record or record request.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter is directed to systems and methods for transferring medical image records. For example, a method for transferring a medical image record includes receiving, by one or more computing devices and from a client device of a first user, a query for the medical image record stored within a record storage system, the medical image record having one or more characteristics. The method includes selecting, by the one or more computing devices, a transfer protocol for transferring the medical image record from the record storage system based on at least one of the characteristics of the medical image record or record request, or both. The method further includes transferring, by the one or more computing devices, the medical image record using the transfer protocol; and sending the medical image record to the client device of the first user for display.

The record storage system can be a picture archiving and communication system (PACS). In particular embodiments the storage system can be a Vendor Neutral Archive (VNA). The medical image record can be one or more Digital Imaging and Communications in Medicine (DICOM) Service-Object Pair (SOP) Instances. The DICOM SOP Instances can be in one or more Series inside one or more Studies. At least one characteristic can be a number of DICOM SOP Instances. At least one characteristic can be an image type. In particular embodiments the image type can be one of an X-ray CR type, a CT type, an MRI type, an ultrasound type, one of dozens of other types recognized by the DICOM standard (see for example DICOM C.7.3.1.1, http://dicom.nema.org/dicom/2013/output/chtml/part03/sect_C.7.html, which is incorporated herein by reference). At least one characteristic can be a size of the medical image record.

The transfer protocol can be selected based at least in part on the number of DICOM SOP Instances. Alternatively, or additionally, the transfer protocol can be selected based at least in part on the image type. Alternatively, or additionally, the transfer protocol can be selected based at least in part on the size of the medical image record. The method can further include querying the record storage system for at least one of the characteristics of the medical image record and the transfer protocol can be selected based on the at least one characteristic of the medical image record or at least one characteristic of the medical image record request, or both.

Selecting the protocol can include selecting one of a Transmission Control Protocol (TCP) connection and a HyperText Transfer Protocol/HyperText Transfer Protocol Secure (HTTP/S) connection. Selecting the protocol can include selecting one of a DICOM messaging protocol and a DICOM web services protocol.

The method can include caching the medical image record. The method can include transferring one or more additional medical image records associated with the medical image record and/or the medical image record request and caching the additional medical image records. The method can include receiving, by the one or more computing devices and from the client device of the first user, a unique identifier associated with the record storage system.

As further disclosed herein, one or more computer-readable non-transitory storage media embodying software are provided. The software is operable when executed to receive, by the one or more computing devices and from a client device of a first user, a query for a medical image record stored within a record storage system, the medical image record having one or more characteristics; select, by the one or more computing devices, a transfer protocol for transferring the medical image record from the record storage system based on at least one of the characteristics of the medical image record; transfer, by the one or more computing devices, the medical image record using the transfer protocol; and send the medical image record from the one or more computing devices to the client device of the first user for display.

As further disclosed herein, a system including one or more processors and a memory coupled to the processors having instructions executable by the processors is provided. The processors are operable when executing the instructions to: receive, by the one or more computing devices and from a client device of a first user, a query for a medical image record stored within a record storage system, the medical image record having one or more characteristics; select, by the one or more computing devices, a transfer protocol for transferring the medical image record from the record storage system based on at least one of the characteristics of the medical image record; transfer, by the one or more computing devices, the medical image record using the transfer protocol; and send the medical image record from the one or more computing devices to the client device of the first user for display.

DRAWINGS

DETAILED DESCRIPTION

Reference will now be made in detail to the various exemplary embodiments of the disclosed subject matter, exemplary embodiments of which are illustrated in the accompanying drawings. The methods and systems described herein can be used for transferring medical image records, such as medical records stored on a picture archiving and communication system (PACS). A variety of records are suitable for retrieval by the present disclosure and the records can be stored in any system, for example a Vendor Neutral Archive (VNA). For purpose of illustration and not limitation, the systems and methods are described herein with respect to transferring medical image records (referred to hereinafter as "medical image records" or "records"), specifically DICOM records, stored on a PACS system using Digital Imaging and Communications in Medicine (DICOM) messaging services and DICOM web services, however the methods and system herein can be used for transferring digital records using any transfer protocols. As used in the description and the appended claims, the singular forms, such as "a," "an," "the," and singular nouns, are intended to include the plural forms as well, unless the context clearly indicates otherwise. Accordingly, as used herein, the term medical image record can refer to one medical image record or a plurality of medical image records. For example, as referred to herein a medical image record can include a single DICOM SOP Instance, one or more DICOM SOP Instances in one or more Series, one or more Series inside one or more Studies, and one or more Studies.

Figure 1:
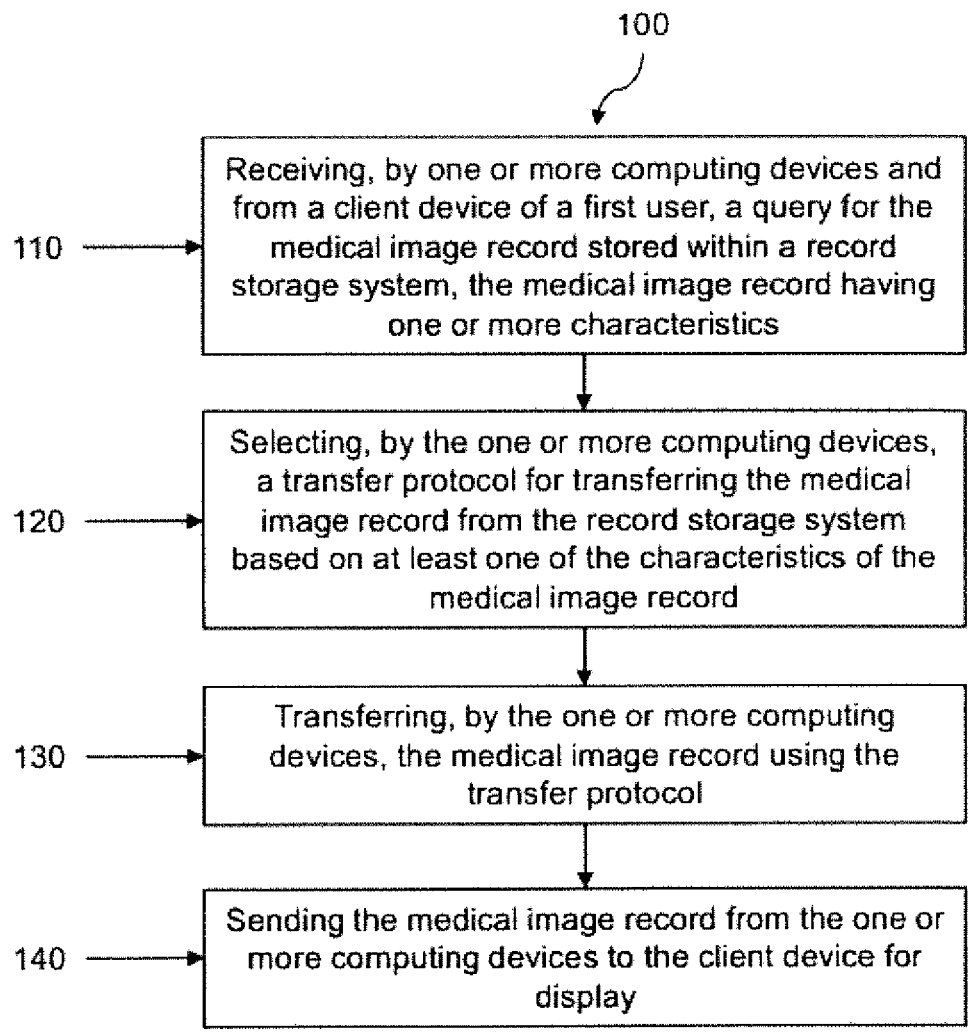
FIG. 1 is a flow chart of a method for transferring medical image records in accordance with the disclosed subject matter.
Figure 2:
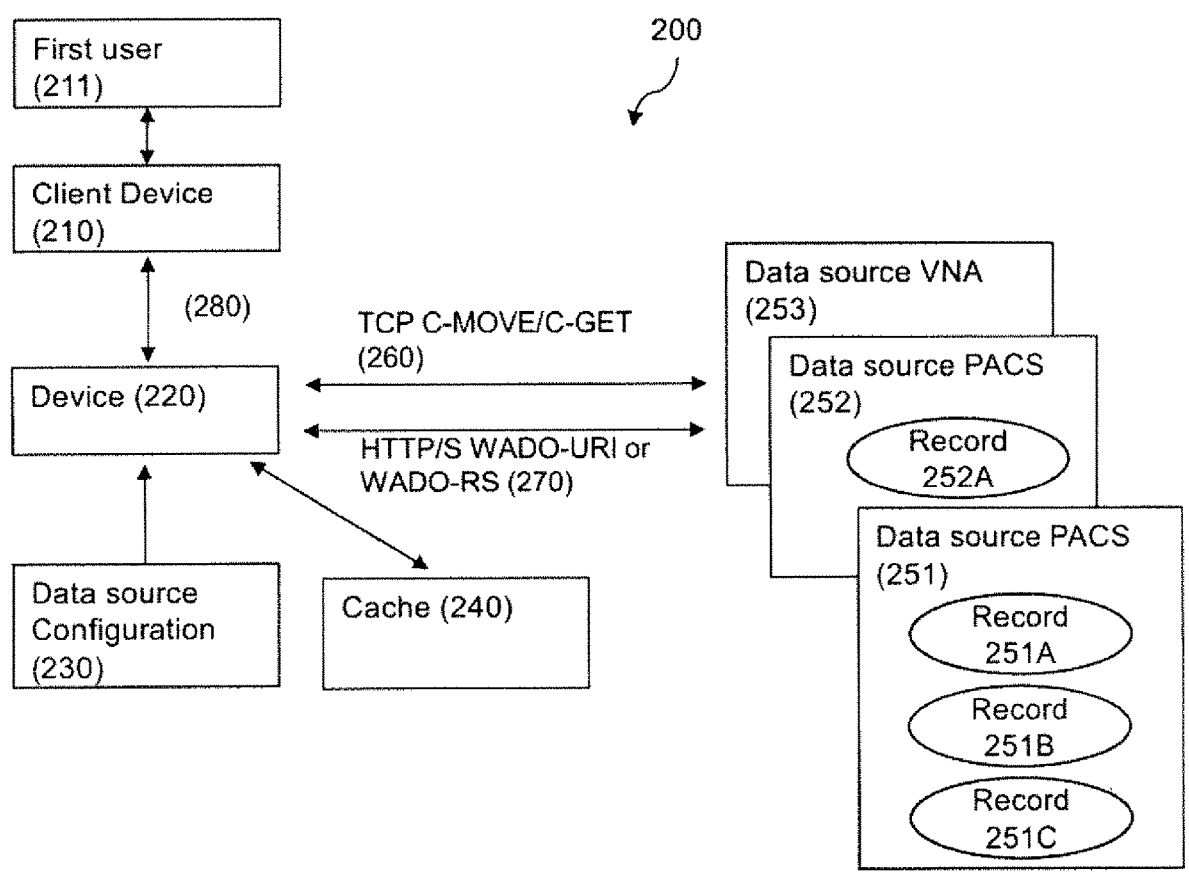
FIG. 2 is a diagram showing the schematic configuration of a medical information network including a system for transferring medical image records in accordance with the disclose subject matter.

Referring to FIGS. 1 and 2 for the purpose of illustration and not limitation, the disclosed method (100) can be implemented on medical information network 200. The medical information network 200 can include client device 210. The client device 210 can be a workstation or web browser for a user 211, for example a medical professional. The workstation can be a computer and can have a known hardware configuration, such as a CPU, a main storage device, an auxiliary storage device, an input/output interface, a communication interface, and input device, a display device and a data bus. A known operating system or the like can be installed on the workstation 211. When client device 210 is a web browser, the medical record requests can be made directly from the command line or from within a medical application web page that provides a user interface for querying and viewing medical records. The medical information network 200 can include a device 220, which can be one or more computing devices coupled to the client device 210 by interface or query 280. The medical information network 200 can also include data source configuration 230, cache 240, and data sources 251, 252, 253, which store medical image records 251A, 251B, 251C, 252A. The data sources 251, 252, and 253 can be any type of data source. For example, data sources 251, 252 can be PACS systems and data source 253 can be a VNA data source. Records 251A, 251B, 251C, 252A can be DICOM objects, such as one or more SOP Instances, Series, or Studies. The medical image records 251A, 251B, 251C, 252A can be transferred from the data sources 251, 252, 253 to the device 220 using transfer protocols 260 or 270. The medical image records 251A, 251B, 251C, 252A can then be sent to the user device 210 for presentation to the user 211. The medical image records 251A, 251B, 251C, 252A can also be stored in cache 240 for quicker retrieval for repeated requests. One or more elements of the medical information network 200 can be physically coupled, coupled by a network such as a local area network, or coupled through the Internet or a dedicated circuit. The network can be a network that is capable of realizing high-speed transfer of medical image records, such as an optical network.

The method (100) can include receiving (110), by one or more computing devices 220 and from a client device 210 of a first user 211 a query 280 for a record 251A stored within a record storage system 251, the record 251A having one or more characteristics. The first user 211 can be, for example, a medical professional. The client device 210 can be a medical workstation, web browser, or web application. The query 280 can be web based using HyperText Transfer Protocol/HyperText Transfer Protocol Secure (HTTP/S) or via a coded API between client device 210 and device 220 such as COM or an internal function call when client device 210 and device 220 exist within the same computing process.

The query 280 can include information about, or identifying characteristics of, record 251A, for example, a unique name, number, or location. Common query DICOM characteristics to identify record 251A can include one or more SOP Instance unique identifier (UID), Series (UID), or Study (UID); the size of the record (i.e., number of bytes that the record uses); the modality type of the record (as described in greater detail below); or other features of the record 251A, including creation date, physician name or ID, patient name or ID, and patient gender. In particular embodiments, the method can include querying the record storage system 251 for additional characteristics of the record 251A. For example, commands such as DICOM C-FIND and DICOM QIDO-RS can be used by device 220 to query the record storage system 251 before selecting transfer protocol 260 or 270 for record transfer The record storage systems 251, 252, 253 can be a PACS or VNA and the medical image record 251A can be one or more DICOM objects, also called Service-Object Pair (SOP) Instances. DICOM SOP Instances are contained within a Series, and one or more Series are contained within a Study. As referred to herein, the medical image record 251A can refer to a single DICOM SOP Instance or a plurality of DICOM SOP Instances (for example, 10,000 CT scans), and the medical image record 251A can be one or more DICOM SOP Instances, Series, or Studies. Examples of medical image record types include an X-ray CR, CT scan, MRI, ultrasound image, or other modalities defined by DICOM Standard C.7.3.1.1. The record 251A can also have a particular size, which refers to the number of bytes that the record uses when stored. A single DICOM SOP Instance can range from a few KB for a short Structured Report (SR) to an upper limit of 4 GB. The 3D Mammogram instances (breast tomosynthesis or "TOMO") are frequently above 1 GB in size. Accordingly, Series or Studies can be orders of magnitude larger as they can contain hundreds or thousands of SOP instances.

The disclosed method can include selecting (120), by the one or more computing devices 220, a transfer protocol 260, 270 for transferring the record 251A from the data source PACs 251 based on at least one of the characteristics of the record 251A or of the record request. In particular embodiments, selecting a transfer protocol can include selecting one of a TCP connection 260 or a HTTP/S connection 270. For example, selecting the transfer protocol can include selecting one of a DICOM messaging protocol 260, such as C-MOVE or C-GET operations, or a DICOM web services protocol 270, such as Web Access for DICOM Objects (WADO) operations, including WADO-RS or WADO-URI. Selecting between DICOM protocols can lead to improved transfer of files. DICOM messaging protocols are better suited for transferring a large number of DICOM SOP Instances due to better error handling with automatic retries when SOP Instances fail to transfer and detailed reporting with number of records found and number of records moved successfully. The DICOM web services protocols (WADO) treat the medical record as one delivery element, do not include automated retries, and the only success status provided is HTTP result codes (i.e., codes 204 (no content), 200 (success) or 206 (partial content delivered)). Also, HTTP/S transfer rates slow down with large content sizes (hundreds of megabytes and above) due to web buffering, while TCP streams data and is not impacted by size. Accordingly, the disclosed methods and systems allow for improved performance when transferring DICOM objects by using the transfer protocol best suited for transferring a particular DICOM object, based on certain characteristics of the DICOM object, for example, the size of the medical image record 215A.

Selecting the transfer protocol can be based on one or more characteristics of the requested record 251A or record query 280. Any characteristic of the record or request that can be used as a proxy for the size of the record can be used for selecting the transfer protocol. For example, one characteristic of the request that can be used as a proxy for the size of the record is whether it is a single DICOM SOP Instance, Series, or Study. As an example, and not by way of limitation, if the requested record only includes a single DICOM SOP Instance, device 220 can utilize a DICOM web services protocol 270. If a Series or Study is requested, a DICOM messaging protocol 260 can be used. Alternatively, or additionally, selecting the transfer protocol can be based on the number of DICOM SOP Instances. For example, if query 280 allows for multiple SOP Instance UIDs to be specified, device 220 can select a DICOM web services protocol 270 if the number of DICOM SOP Instances is below a threshold (e.g., 1,000), and a DICOM messaging protocol 260 if the number is above the threshold. Alternatively, or additionally, device 220 can query the source 251 (using DICOM C-FIND or QIDO-RS) for the number of SOP Instances matching the client's query 280 and select the protocol based on the number of instances located as described above. Since size of DICOM Instances can vary widely by modality type, particular embodiments can include a table of record number thresholds based upon modality type. As an example, and not by way of limitation, the number threshold for CT type can be 1000 while the threshold for TOMO type can be 1.

In particular embodiments selecting the transfer protocol can be based on the image type of the record 251A, which can be a proxy for predicting the medical record size. For example, and not by way of limitation, 3D Mammograms can reach sizes of 2 GB or more, which can be overwhelming for a web transfer, particularly when HTTPS is used, and the entire Study must be downloaded and buffered before it can be decrypted. Accordingly, if a type of image that is known to be large (such as a TOMO type record) is requested, a DICOM messaging protocol 260 can be selected for transferring the record. If an image type that is known to typically be small is requested, such as modalities CR or CT, DICOM web services protocol 270 can be selected for transferring the record. In particular embodiments, device 220 can include a table of image types identified in DICOM C.7.3.1.1 with the preferred protocol 260, 270 indicated for each type.

Additionally, or alternatively, selecting the transfer protocol can be made based on the size of the requested record (251A). If a record has a size smaller than a threshold, for example, and not by way of limitation, 50 megabytes, a DICOM web services protocol 270 can be used, and if a record has a size greater than the threshold, a DICOM messaging protocol 260 can be used. As disclosed herein, selecting the transfer protocol can be based on any combination of the characteristics described hereinabove or any other characteristics of the record or request.

The method can include transferring (130), by the one or more computing devices 220, the record 251A, using the selected transfer protocol 260, 270. For example, the record can be transferred from the storage system 251 to the one or more computing devices 220. In particular embodiments, the method can include caching the record 251A. For example, after the record 251A has been transferred, it can be stored in a cache 240. This can allow a faster response to repeat queries. Storage in the cache 240 can be triggered by any characteristics of the record 251A, for example, the number of Instances, size, or type of the record 251A. For example, caching DICOM web requests above 50 megabytes in size to avoid re-transferring a repeated request. In some embodiments caching the record 251A can be triggered by the protocol used to transfer the record 251A. For example, DICOM message requests can be cached while DICOM web request are not. Some embodiments can use one or more methods to determine whether a record should be cached. For example, the method can include caching all DICOM message requests while caching only large DICOM web requests. In some embodiments, the method can include transferring one or more additional records 251B, 251C associated with the record 251A, and caching the additional records 251B, 251C. For example, if the user 211 only requests a single DICOM SOP Instance that is part of a Series or Study, device 220 can use protocol 260 so that the remaining DICOM SOP Instances in the Series or Study can be transferred and cached. As another example, device 220 can use protocol 260 to transfer and cache prior historical studies for the same patient. This can pre-load the cache 240 for better performance if a user 211 requests to see additional related records, even if only one record was initially requested. Caching the record 251A can be configurable as an option based on the data source 251, 252, 253.

The method can further include sending (140) the record 251A from Device 220 to the client device 210 of the first user 211 for display.

In particular embodiments, the method can include receiving, by the one or more computing devices 220 and from the client device 210 of the first user 211, a unique identifier associated with the record storage system 251, 252, 253. For example, DICOM data sources are typically identified by Application Entity Titles (AeTitle) but any string or unique identifier could be used to identify a specific record storage system 251, 252, 253. Information regarding the specific data sources can be stored in the data source configuration 230. The one or more computing device 220 can have sufficient information from data source configuration 230 for employing DICOM C-MOVE\C-GET or DICOM web services on the data source. This can include host, port, web protocol, client AeTitle, and PACS AeTitle. In particular embodiments, device 220 selecting the transfer protocol 260, 270 can be based on the data source configuration 230 of the requested data source 251, 252, 253.

As an example, for purpose of illustration and not limitation, in operation, a user 211 can make a request for a medical image record 251A. The requested digital medical image can be a Study including 10,000 CT scans. The request can be made at the user device 210 using interface 280 to send a generic function call for the Study (i.e., not a DICOM messaging operation or a DICOM web services protocol). Upon receiving the request, the device 220 can check the cache 240 and deliver the record from cache if found. If not in cache 240, device 220 can select a DICOM messaging protocol because the request is for a Study and the expected record size is large. The DICOM configuration for C-GET request for source 251 is read from data source configuration 230 and executed. The device 220 receives the record 251A from PACS 251. The user 211 is not necessarily aware or alerted that the record was transferred using a DICOM messaging protocol. The record 251A can then be sent to the client device 210 for display to the user 211. The record 251A can also be cached in cache 240 because DICOM messaging was used.

As another example, for purpose of illustration and not limitation, in operation, a user 211 can make a request using client device 210 via query 280 for a medical image record 252A. The requested digital medical image can be a single DICOM SOP Instance of an X-ray. The request can also include a unique identifier for a specific data source 252. Upon receiving the request, the device 220 can check cache 240 and determine that the record 252A is not stored in the cache 240. Device 220 then can select a DICOM web services protocol, because the request is for a single DICOM SOP Instance. The user 211 is not necessarily aware or alerted that a DICOM web services protocol was selected. The device 220 can further use data source configuration 230 to identify the WADO URL associated with data source 252 corresponding with the unique identifier provided by the user 211. The device 220 can receive the record 252A from PACS 252 using DICOM web services operation WADO-RS 270. The record 252A can then be sent to the client device 210 for display to the user 211. After receiving record 252A from WADO, device 220 can determine that the size is above the threshold of 50 megabytes and can store a copy of record 252A to cache 240 to avoid future delays in transferring the large record.

The flowcharts and block diagrams illustrate the architecture, functionality, and operation of possible implementations of systems, methods, and computer program products according to various embodiments of the disclosed subject matter. In this regard, each block in the flowcharts or block diagrams may represent a module, segment, or portion of code, which comprises one or more executable instructions for implementing the specified logical function(s). It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

Furthermore, plural instances can be provided for components, operations or structures described herein as a single instance. Boundaries between various components, operations and data stores are somewhat arbitrary, and particular operations are illustrated in the context of specific illustrative configurations. Other allocations of functionality are envisioned and can fall within the scope of the disclosure(s). In general, structures and functionality presented as separate components in exemplary configurations can be implemented as a combined structure or component. Similarly, structures and functionality presented as a single component can be implemented as separate components.

As described above in connection with certain embodiments, certain components, e.g., device 220, can include a computer or computers, processor, network, mobile device, cluster, or other hardware to perform various functions. Moreover, certain elements of the disclosed subject matter can be embodied in computer readable code which can be stored on computer readable media and which when executed can cause a processor to perform certain functions described herein. In these embodiments, the computer and/or other hardware play a significant role in permitting the system and method for displaying medical image records. For example, the presence of the computers, processors, memory, storage, and networking hardware provides the ability to display medical image records in a more efficient manner. Moreover, the display of medical image records, cannot be accomplished with pen or paper, as such information is received over a network in electronic form.

Additionally, as described above in connection with certain embodiments, certain components can communicate with certain other components, for example via a network, e.g., a local area network or the internet. To the extent not expressly stated above, the disclosed subject matter is intended to encompass both sides of each transaction, including transmitting and receiving. One of ordinary skill in the art will readily understand that with regard to the features described above, if one component transmits, sends, or otherwise makes available to another component, the other component will receive or acquire, whether expressly stated or not.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A method for transferring a medical image record, comprising:
   receiving, by one or more computing devices and from a client device of a first user, a query for the medical image record stored within a record storage system, the medical image record having a size, and one or more characteristics, each characteristic being a proxy for the size to suggest if the size the record is above a size threshold or below the size threshold;
   selecting, by the one or more computing devices, a transfer protocol for transferring the medical image record from the record storage system based on at least a first characteristic of the one or more characteristics of the medical image record;
   transferring, by the one or more computing devices, the medical image record using the transfer protocol; and
   sending the medical image record to the client device of the first user for display;
   wherein the transfer protocol is a Digital Imaging and Communications in Medicine (DICOM) messaging protocol if the first characteristic suggests the size of the medical image record is above the size threshold; and
   wherein the transfer protocol is a DICOM web services protocol if the first characteristic suggests the size of the medical image record is below the size threshold.

2. The method of claim 1, wherein the record storage system comprises a picture archiving and communication system (PACS).

3. The method of claim 1, wherein the medical image record comprises one or more Digital Imagining and Communications in Medicine (DICOM) Service-Object Pair (SOP) Instances.

4. The method of claim 3, wherein at least one characteristic comprises a number of DICOM SOP Instances.

5. The method of claim 4, wherein the transfer protocol is selected based at least in part on the number of DICOM SOP Instances.

6. The method of claim 1, wherein at least one characteristic comprises an image type.

7. The method of claim 6, wherein the image type is one of an X- ray CR type, a CT type, an MRI type, and an ultrasound type.

8. The method of claim 6, wherein the transfer protocol is selected based at least in part on the image type.

9. The method of claim 1, wherein selecting comprises selecting one of a Transmission Control Protocol (TCP) connection and a HyperText Transfer Protocol/HyperText Transfer Protocol Secure (HTTP/S) connection.

10. The method of claim 1, further comprising caching the medical image record.

11. The method of claim 1, further comprising transferring one or more additional medical image records associated with the medical image record and caching the additional medical image records.

12. The method of claim 1, further comprising querying the record storage system for at least one of the characteristics of the medical image record.

13. The method of claim 12, wherein the transfer protocol is selected based on the at least one characteristic of the medical image record.

14. The method of claim 1, further comprising receiving, by the one or more computing devices and from the client device of the first user, a unique identifier associated with the record storage system.

15. One or more computer-readable non-transitory storage media embodying software that is operable when executed to:
   receive, by the one or more computing devices and from a client device of a first user, a query for a medical image record stored within a record storage system, the medical image record having a size, and one or more characteristics, each characteristic being a proxy for the size to suggest if the size the record is above a size threshold or below the size threshold;
   select, by the one or more computing devices, a transfer protocol for transferring the medical image record from the record storage system based on at least a first characteristic of the one or more characteristics of the medical image record;
   transfer, by the one or more computing devices, the medical image record using the transfer protocol; and
   send the medical image record from the one or more computing devices to the client device of the first user for display;
   wherein the transfer protocol is a Digital Imaging and Communications in Medicine (DICOM) messaging protocol if the first characteristic suggests the size of the medical image record is above the size threshold; and
   wherein the transfer protocol is a DICOM web services protocol if the first characteristic suggests the size of the medical image record is below the size threshold.

16. A system comprising: one or more processors; and a memory coupled to the processors comprising instructions executable by the processors, the processors being operable when executing the instructions to:
   receive, by the one or more computing devices and from a client device of a first user, a query for a medical image record stored within a record storage system, the medical image record having a size, and one or more characteristics, each characteristic being a proxy for the size to suggest if the size the record is above a size threshold or below the size threshold;
   select, by the one or more computing devices, a transfer protocol for transferring the medical image record from the record storage system based on at least a first characteristic of the one or more characteristics of the medical image record;
   transfer, by the one or more computing devices, the medical image record using the transfer protocol; and
   send the medical image record from the one or more computing devices to the client device of the first user for display;
   wherein the transfer protocol is a Digital Imaging and Communications in Medicine (DICOM) messaging protocol if the first characteristic suggests the size of the medical image record is above the size threshold; and wherein the transfer protocol is a DICOM web services protocol if the first characteristic suggests the size of the medical image record is below the size threshold.

\* \* \* \* \*